United States Patent
Gazzano

(10) Patent No.: US 9,127,668 B2
(45) Date of Patent: Sep. 8, 2015

(54) APPARATUS FOR FLOWING FLUIDS

(75) Inventor: Michele Gazzano, Trezzano sul Naviglio (IT)

(73) Assignee: HEMODEC S.R.L., Salerno (IT)

( * ) Notice: Subject to any disclaimer, the term of this patent is extended or adjusted under 35 U.S.C. 154(b) by 281 days.

(21) Appl. No.: 13/702,314

(22) PCT Filed: Jun. 5, 2011

(86) PCT No.: PCT/IB2011/001214
§ 371 (c)(1),
(2), (4) Date: Dec. 6, 2012

(87) PCT Pub. No.: WO2011/154796
PCT Pub. Date: Dec. 15, 2011

(65) Prior Publication Data
US 2013/0084200 A1    Apr. 4, 2013

(30) Foreign Application Priority Data
Jun. 7, 2010   (IT) .............................. BO2010A0353

(51) Int. Cl.
*F04B 43/08* (2006.01)
*A61M 1/16* (2006.01)
*A61M 1/34* (2006.01)
*A61M 1/36* (2006.01)

(52) U.S. Cl.
CPC ................ *F04B 43/086* (2013.01); *A61M 1/16* (2013.01); *A61M 1/34* (2013.01); *A61M 1/36* (2013.01); *A61M 2205/122* (2013.01); *A61M 2209/084* (2013.01)

(58) Field of Classification Search
CPC ..... F04B 43/086; F04B 43/082; F04B 43/088
USPC ................ 417/475, 478, 479, 477.2; 604/153
See application file for complete search history.

(56) References Cited

U.S. PATENT DOCUMENTS

| | | | | |
|---|---|---|---|---|
| 4,468,222 | A | * | 8/1984 | Lundquist ..................... 604/153 |
| 4,998,914 | A | * | 3/1991 | Wiest et al. ..................... 604/67 |
| 2009/0016915 | A1 | * | 1/2009 | Caramuta .................. 417/477.2 |
| 2009/0035152 | A1 | * | 2/2009 | Butterfield ...................... 417/53 |
| 2009/0092507 | A1 | * | 4/2009 | Ramirez et al. ............ 417/410.1 |

* cited by examiner

*Primary Examiner* — Charles Freay
(74) *Attorney, Agent, or Firm* — Mark M. Friedman

(57) ABSTRACT

Apparatus for the treatment of the blood, comprising at least one pump (25, 26, 27), matchable with a corresponding portion of tube (35, 36, 37) supported by a cartridge or module (3) which is associated to the apparatus (1), characterized in that it comprises a pump capable of reducing the pressure inside the chamber defined by the association of the cartridge (3) to the apparatus (1).

16 Claims, 6 Drawing Sheets

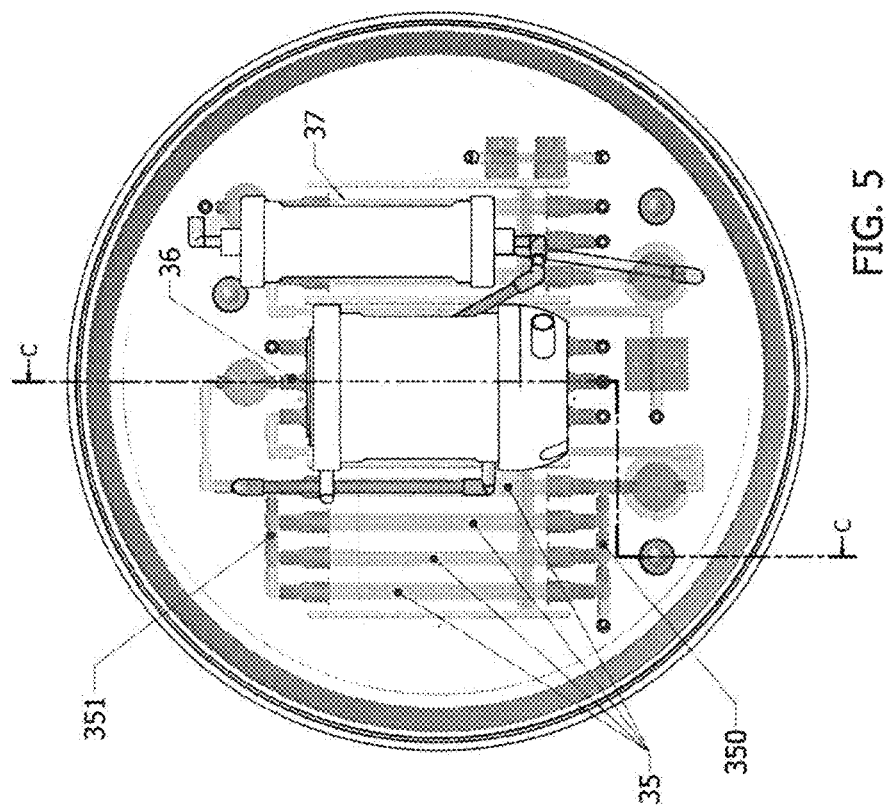
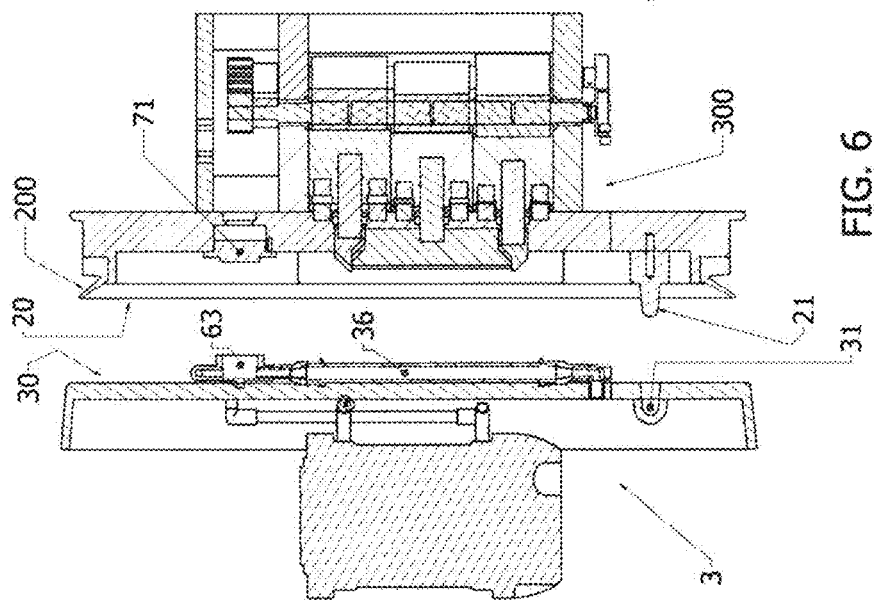
FIG. 5
FIG. 6

APPARATUS FOR FLOWING FLUIDS

The present invention relates to an apparatus for the treatment of the blood.

The technical field of the invention is the medical/hospital field, and, in particular, relates to the problem of preparing dialysis machines, machines for haemofiltration, for the so-called decapneization and, more generally, for all the apparatuses which, including one or more peristaltic pumps and/or syringe pumps, require complicated preparation procedures which need, among other things, the placement of the "under-pump" tubes in the correct operating position and the accommodation in suitable supports of haemofilters, oxygenators and other components of the circuit, connected by means of a not simple network of connections of hoses, drippers, debubblers, pressure sensors, temperature sensors, heaters and more.

In particular, the apparatus of the invention comprises a pump and a module or cartridge, preferably of disposable type. An apparatus of this type is described in WO2006/103711. This document describes an apparatus that includes a series of peristaltic pumps and a cartridge, and that simplifies the operation and the start-up of known procedures, reducing the time and the risk of mounting errors.

One of the aims of the present invention is to eliminate substantially absolutely the risk of incorrect assembly, with advantages deriving from the simplification of use, which speeds up the start of treatment to be performed, safely, and limiting the need for highly skilled personnel.

Another advantage of the present invention is provided by the improved pumping capacity due to the fact that the part of the tubes intended to be pressed is placed inside a chamber having a pressure lower than atmospheric, so determining a most effective operation of the tube and a longer life thereof.

In addition, the apparatus of the invention allows a reduction of filling volume of the circuit (priming), thanks to the optimizing and the shortness of the connections, together with a reduced hemolysis due to the particular operation of the peristaltic pump; the pump for the blood of this apparatus, as discussed in detail below, also allows an outflow very linear and homogeneous.

Further advantages of the present invention are listed below.

Thanks to the depressurization obtained inside of a chamber defined by a module or cartridge with the apparatus, it is possible to get a powerful matching force between the components; for example, using a module with a diameter of 40 cm, subtracting only a half of the atmospheric pressure, is obtained a force greater than 600 kg.

The force exerted on the tube to produce the pumping is absolutely homogeneous, with an uniform consistency over the entire surface, with total absence of more stressed points, i.e. points more subject to breakage; such feature is also useful for mating with accessories.

By the clamping "by-pressure" between the module and the apparatus it is possible to obtain a greater accuracy and fewer complications related to the locking of the module compared to systems based on mechanical locking.

It has also increased the efficiency of filling (suction) of under-pump tubes, on the contrary in respect to traditional pumps where the suction is totally entrusted to the elastic memory of the under-pump tube which, at the end of the discharge of the pump, tends to return to its original shape.

There is a constancy in the time of the performances of the pump; in fact, since the pump is controlled during both pumping phase (active) and in the suction phase (which is passive in traditional pumps) the performances do not diminish with use, even if the elastic memory of the tube progressively loses.

Thanks to the present invention, it is possible to use thin-walled under-pump tubes. Since the fluid isn't sucked by means of the elasticity of under-pump tubes, but by the vacuum which is around to the tubes, a thin wall allows a faster response, with the following additional advantages:

with the same outer diameter the tube allows an inside diameter considerably larger and therefore a greater volume of fluid in the section of under-pump tube; this means more effective pumping action at the same rpm of the engine, or a solution that allows a lower hemolysis, a slower and less traumatic speed for the same desired flow;

it is required less force to compress the tube, due to its higher yielding; this allows a greater life of the tube that is subjected to less stress, and also a smaller effort of the engine which drives the pumps is required, and then, in cascade, a greater durability of all mechanical components involved is obtained.

This result was reached in accordance with the invention by adopting the idea of a machine having the features described in claim 1. Other features are in dependent claims.

Among the advantages of the present invention there are: the procedures of preparation and the start of blood processing apparatuses are extremely simplified; the risk of error is substantially eliminated; the effectiveness and durability of all components of the pump are high; the pressing elements of the pump act on the corresponding portions of the tube in a de-pressurized atmosphere: in this way is improved the efficiency of the pumping and the life of the tube, because the return to the rest configuration of the tubes (not pressed) is facilitated by de-pressurization; these apparatuses can also be used by non-highly qualified personnel; there is a considerable reduction of the priming; it is offered a disposable pump module characterized by a high biocompatibility and reduced hemolysis.

The advantages and features of the invention will be better understood from the following description and with the help of the annexed drawings, given as practical examples of the invention, but not to be considered by limiting, in which:

FIG. 5 is a front view of the base wherein the module is overlapping to the pump unit but is not in use, with transparent parts in order to better highlight others;

FIG. 6 is a sectional view along the line C-C of FIG. 5;

A device 1 in accordance with the invention comprises a base with a pumps unit 2 and a cartridge or module 3.

The pump described and illustrated in the figures can be defined as a "pump-linear", as will be evident from the following description.

Figure 1:
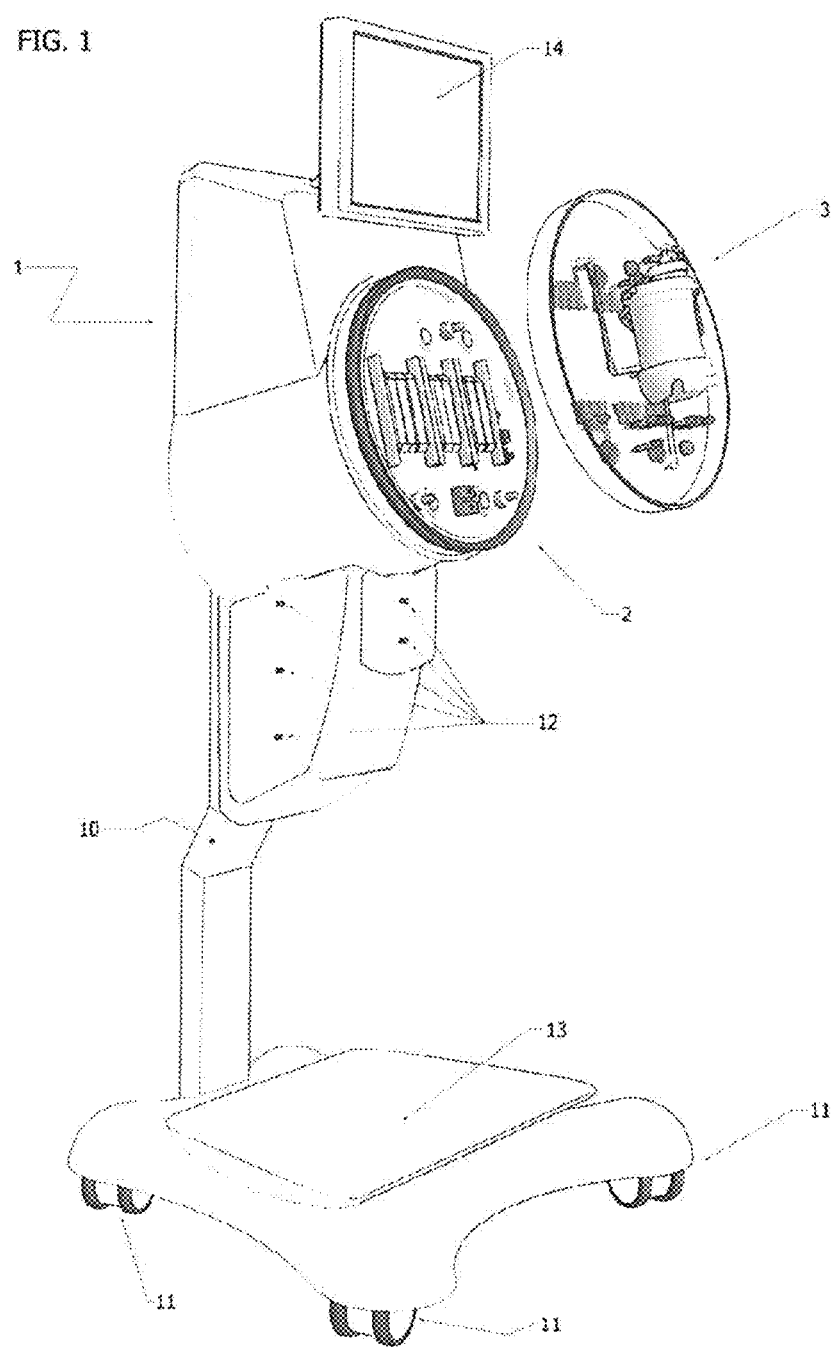
FIG. 1 is a schematic perspective view of an apparatus according to the invention, with the same apparatus placed on a support structure, with a part, relating to the cartridge, shown separated from the base, at whom it is normally associated in condition of use.
Figure 2:
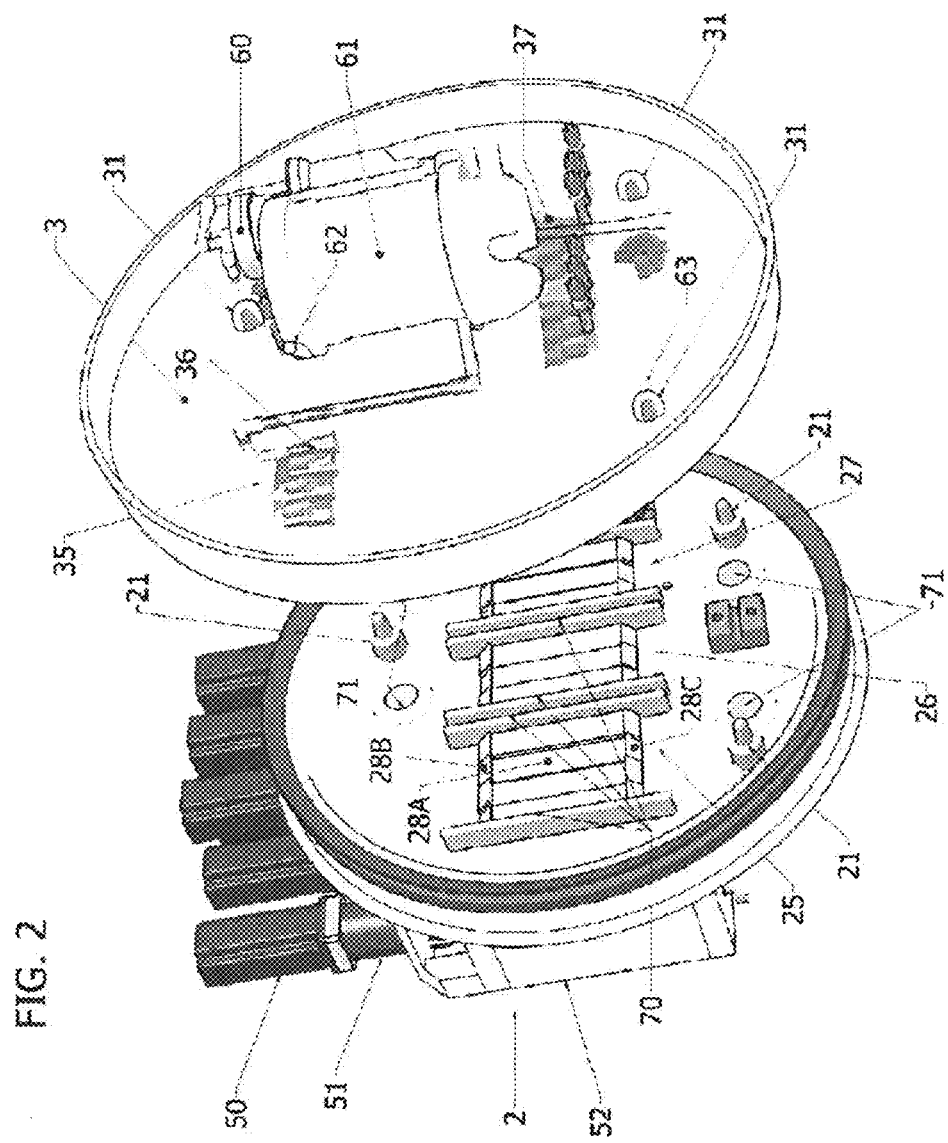
FIG. 2 is a perspective exploded view with parts in transparency in which there are a series of pumps and a cartridge, which are parts of the apparatus, and which are represented in a configuration wherein the cartridge is separated from the pump unit, or in a rest configuration or not of use.
Figure 3:
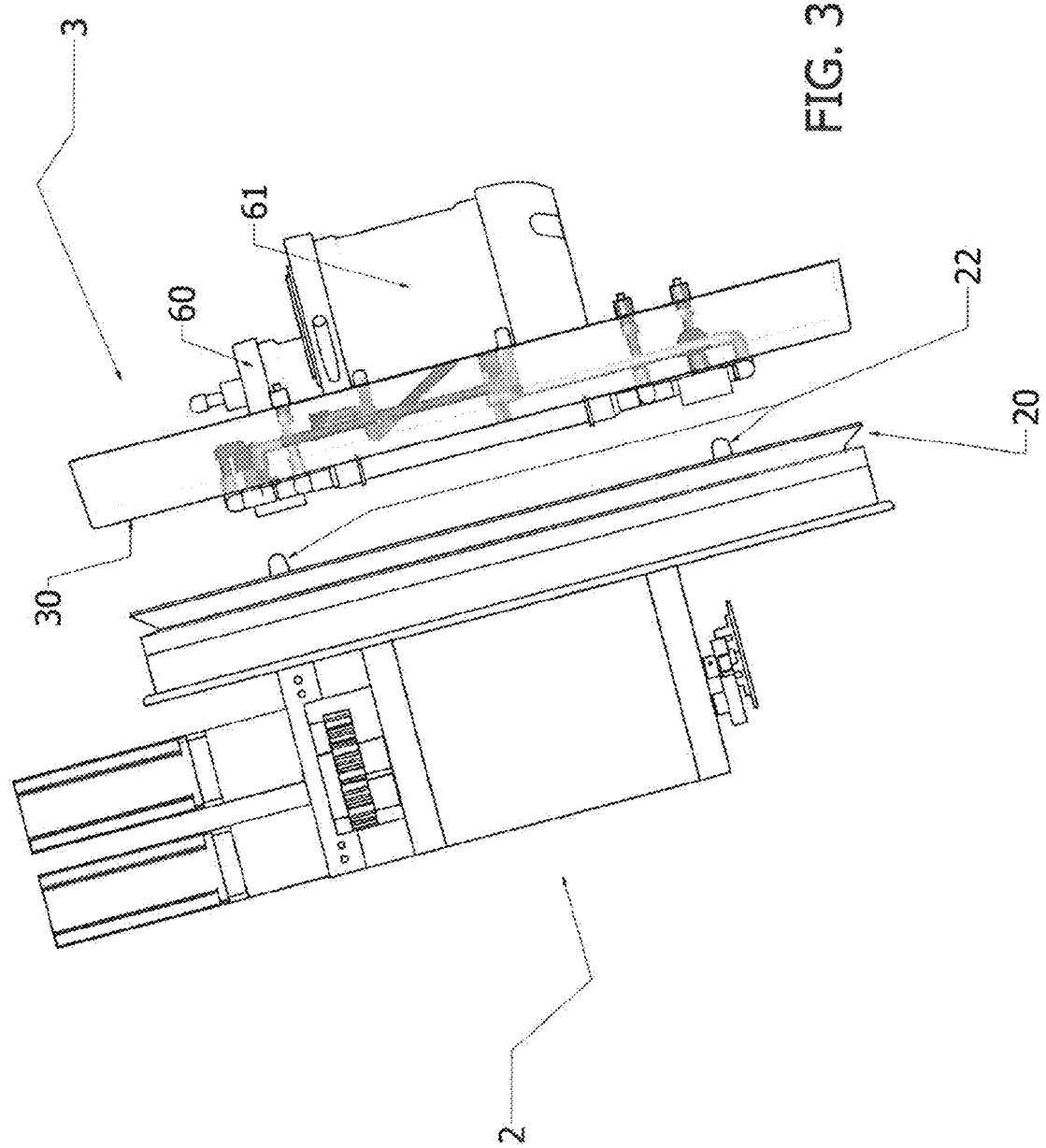
FIG. 3 is a side view with parts in transparency of the pumps and of the cartridge shown in FIG. 2, in a configuration in which these parts are not associated, i.e. in a configuration that is not working.
Figure 4:
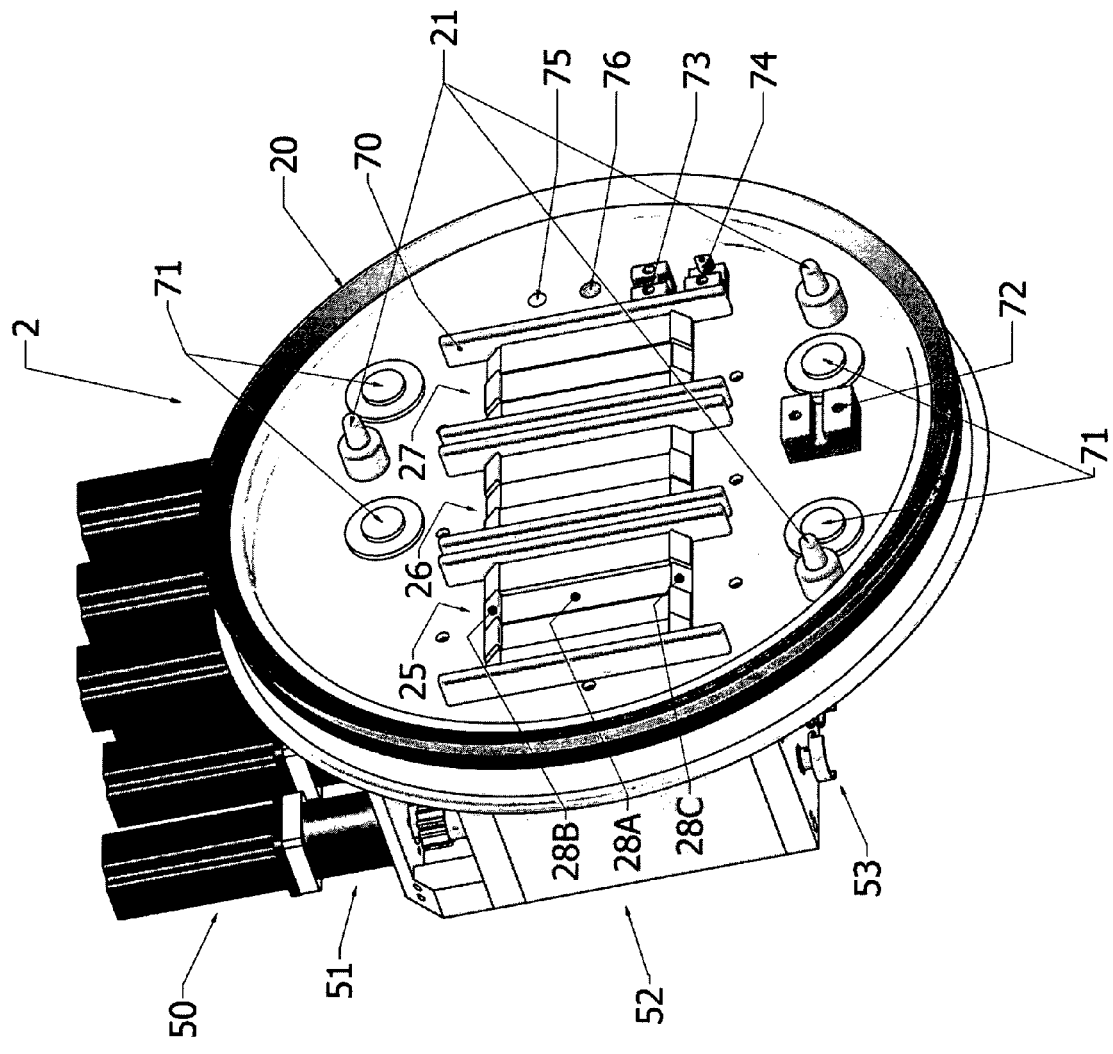
FIG. 4 is a perspective view of a portion of FIG. 2, relating to the base with the pump unit.

In FIG. 1, the apparatus 1 is supported by a support structure 10, which allows it to be available in use and easy to transport thank to the wheels 11 of which is equipped. The support structure 10 is provided with a plurality of pins 12 usable to hang bags and/or other similar containers that are used during therapy. Moreover, advantageously, the structure 10 is provided with a flat area placed inferiorly that defines the plate 13 of a scale; in practice, on the plate 13 can be placed a bag, used for treatment, to be weighed; for example, the bag intended for liquid effluents can be placed on the plate 13 in order to be constantly weighed. The balance is connected to the control system of the machine in order to provide a value that can also be displayed in real time on a video 14 of which the structure 10 is provided.

The term cartridge or module used in this description refers to a preferably disposable container 3, with at least one wall or rigid portion 30. The container contains the components necessary to the therapy procedure and the internal connections, the prepared and/or pre-assembled connections for links external to the patient, the connections for any sub-containers for substances to be infused and connections to containers for waste products to eliminate; in practice the wall 30, as better will be described below, defines the mechanical support to the tubes which is used as reaction plan for the effort of the peristaltic pumps contained in the pump unit 2, which is the base on which the cartridge 3 is associated. All internal components of the disposable module and external connections are pre-assembled, so be ready for use.

In particular, the disposable module 3, which can be formed, for example, in rigid and transparent plastic, is fixed to the base of the pump unit 2, unit that is integral with the 30 fixed part of the apparatus 1, supported by the base 10 in FIG. 1. In the particular example shown, the pump unit 2 and the cartridge 3 have a substantially circular shape in plan. As will be described further below, the circular shape, which determines the absence of corners, or short-range fittings, is a solution that enables an excellent airtight seal (described below). The fit between the cartridge 3 and the pump unit 2 allows an operational connection which can exchange data by means of pressure and temperature sensors, detectors of air bubbles, of blood, etc., and also allows the movement of liquids contained or passing through the module 3 thanks to a peristaltic pumps system with "front access" that, not requiring manual intervention for their preparation, can work as soon it has been connected with the pump unit 2.

In the example shown, the cartridge 3 is provided with three seats 31 arranged at the vertices of a scalene triangle.

On the pumps unit there are three positioning elements or spacers 21 are also arranged at the vertices of a triangle which is corresponding and equal to the triangle defined by the seats 31 of the cartridge 3. In particular, the positioning elements 21 are provided with tapered ends 22 which are complementary shaped with respect to the cavities of the seats 31, in order to be received in the same cavities of seats 31, determining the correct alignment between the two elements 2 and 3. The particular arrangement of the three seats 31 and of the three positioning elements 21 allows a unique matching. This feature absolutely prevents the wrong coupling between the two elements. In other words, it is not possible during the preparation of the apparatus by the operators, to couple to the cartridge pump incorrectly because the three spacers 21 should not enter the premises 31 of the cartridge 3. In the example shown evidence seats 31 and 21 are arranged at a scalene triangle, but you can keep the advantage of this feature with a different arrangement of the invention, provided they fulfill the requirement of uniqueness in coupling. The solution with a triangle with three different sides is advantageous because with the three points defined by the spacers is defined a plan. The correct positioning of the cartridge 3 on the base 2 can also be obtained, however, by means of other kinds of positioning elements and/or systems for detecting the position of mechanical and/or electronic type, for example, can be used sensors, mechanical guides, special conformations of the base and of the cartridge, etc. In the not limited example, the pumps unit 2 is provided with three sets of peristaltic pumps having a frontal access 25, 26, 27. In particular, the first set 25 includes four pumps arranged in parallel, the second 26 and the third 27 set comprise three pumps which, in the example, form six pumps usable for interacting with corresponding six tubes. On the cartridge 3, for each set of pumps, there is a corresponding set of tube portions 35, 36, 37, which are disposed parallel; said portions, when the cartridge 3 is associated with the pump unit 2, are in contact with the corresponding pumps of each set.

The pumps supported by the base 2 are similar in type to those described in the document WO2006/103711, and therefore will not be described in detail. In this type of peristaltic pump, the element that in the peristaltic pumps is called "rotor", i.e. the part that presses the tube, does not act (as in traditional pumps) against a surface which is part of the pump and according to a radial direction with respect to the rotor, but in a frontal direction (like a frontal cam) against the tube and against the rigid surface 30 which is part of the cartridge 3. Each pump is provided with a plurality of pressing elements or hammer elements 28a, 28b, 28c, which are arranged along the longitudinal development of the portions of tube and which are moved in order to intercept the corresponding points of the portions of the tube determining a peristaltic effect. Each pump consists of three pressing elements, or pressure hammers 28a, 28b, 28c which are moved, in the same way as described in the document WO2006/103711, by means of a system with camshaft 300. In particular, the three pressing elements include a central element 28a, also called pressing element 28a in this description, and two lateral elements 28b and 28c which are shorter that the central element 28a and which can be called valves 28b and 28c in this description; said valves are arranged one upstream and one downstream in respect to the element 28a considering the longitudinal dimension of the tube on which they act, or the relevant generated flow. The camshaft has three cams appropriately shaped to intercept the pressure elements 28a, 28b, 28c to push them to the portions of tube to be pressed or to move away from the same. In practice, the camshaft is driven in rotation by acting on one end by means of motors (represented by engines 50, gearbox 51 and a set of alignment gears 52) to sequentially push the three pressing elements against the respective portions of the tube. The apparatus can be provided with cam elements 53 for the interaction with photocells or similar devices to detect the position.

The pressing elements or hammer elements 28a, 28b, 28c are able to adequately compress the tube portions of the cartridge 3 due to the presence of the rigid wall 30 which, in fact, acts as an "anvil" or reaction plan for the hammer elements, and which is a part of the disposable module. In this case, the central element 28a, which is much longer than the lateral elements 28b and 28c, acts itself as a pump while the two external elements act as valves. In practice, the external elements 28b, 28c fully collapse the tube for occluding it, while the central element 28a presses the tube only to a percentage close to 90%, avoiding damage to the solid components of blood (mostly erythrocytes) and reducing the hemolysis in a greater way if compared to conventional peristaltic pumps.

As mentioned previously, in the embodiment of the invention shown in the drawings, each set of pumps 25, 26, 27 is composed of several pumps (four in the case of pumps 25 and three for pumps 26 and 27). The pumps of the set 25 are acting on corresponding parallel tube sections which, for the group of tubes 35, are joined together upstream and downstream of the area interested by the action of pumps, forming a single input tube and a single output tube. In the drawings has been marked respectively with 350 and with 351 the tube upstream and downstream of the area for the pumping action. Each set of pumps 25, 26, 27 is controlled in a proper sequence of steps so that the pressing elements 28a and the valves 28b, 28c of each of the pumps can interact with their corresponding tube sections of each tubes groups 35, 36, 37. In this way, instead of having an intermittent action, an almost continuous flow is obtained; furthermore, by identifying the flow rate with the average flow, it is possible to maintain the pressure within the values supported by the filters and the other components without any peak pressure corresponding to flow peaks, i.e. without any possibility for causing damage to said components and inducing turbulence which can cause blood clots and other problems. For example, the pumps of set 25 can be used to pump blood, acting on a single tube divided in parallel portions 35, while the pumps of set 26 and set 27 can be used to pump fluids according to the more convenient therapy. As an example, the pumps of set 26 and set 27 may act on the corresponding six tubes, represented by groups of parallel tubes 36 and 37, in which can pass, respectively, heparin, calcium citrate, a dilution fluid, a post-dilution fluid, the ultrafiltrate, the effluent liquid.

On both sides of each set of pumps 25, 26, 27 are provided spacers 70 which in the example are formed by little bars which extend in height to a value greater than the pumps; in practice, the spacers 70 are destined to go in contact with the wall 30 of the cartridge 3, with the function of maintaining the correct distance between base and module. The spacers 70 also have the function of making mechanically more resistant to bending the module in respect to stresses due to pressure; in this way, it is possible to use a material less thick and/or less stiff and therefore more economical.

As mentioned previously, the disposable module 3 may include components to allow the measurement of physiologic parameters, tubes for the connections, "active" components such as haemo-concentrators, oxygenators, blood filters, dialysis filters, control components as possible emitters, de-bubblers, sub-containers to be filled with drugs (e.g. heparin). With reference to the attached drawings figures, the disposable module 3 are provided with other components of a circuit of blood processing, in addition to the portions of tube of the sets 35, 36, 37. In particular, the cartridge can be provided with transducers for pressure, temperature or other variables that should be measured, with other small segments of tube on which closing or clamping devices known as "clamp" can act, or with connectors for oxygen or others. In practice, depending on the type of therapy to be executed, the disposable module 3 will be conveniently provided with appropriate components, such as filtering devices, measuring devices, etc., which are known, and therefore will not be described in detail. The transducers 63 may be formed by membranes that act on corresponding detectors provided on the pump unit, capable of exchanging data with them. The membranes, in practice, can define a physical connection (pneumatic or hydraulic) with the corresponding detector provided on the pump unit 2, described below.

With reference to the example shown, the disposable module 3 is provided with a blood filtering device 60 or haemofilter, with an oxygenating device or decapneizator 61, with a connector 62 to be connected with a corresponding oxygen regulator, and with ducts or tubes which, in a known way, are used to connect incoming and outgoing with the patient in treatment.

Correspondingly, on the pump unit 2, there are pressure sensors 71, blood detectors 72 (which, for example, can act on the tube for the ultrafiltrate), detection of air bubbles in the blood 73, associated with closure device 74 ("clamp") controlled by them.

Again, with reference to the example illustrated, on the pump unit 2 are placed some holes that can be used to fix the same group 2 to the base 10 or for the attachment of components. Furthermore, there are two holes 75 and 76. The hole 75 is connected to a vacuum pump (not shown in the drawings), whose operation will be described later; the hole 76 is used by a pressure switch for detecting the pressure within the chamber defined by the pump unit 2 associated to the cartridge 3.

Advantageously, the pump unit 2 is provided with a seal 20, made of rubber or other suitable material, and disposed along an outer perimeter, at an edge of the cartridge 3. With reference to the example shown, the seal 20 is developed as a circle, by copying the shape of the cartridge 3, in particular by copying the part of the same cartridge designed for contact. As mentioned previously, the particular circular shape allows the removal of any angular seal joints, with the achievement of optimal air-tight characteristics.

The gasket 20 has a cross section that forms a tooth 200, facing the exterior: in this way, when the seal is pressed against the cartridge 3, it is partially deformed so as to further increase the air-tight.

Figure 7:
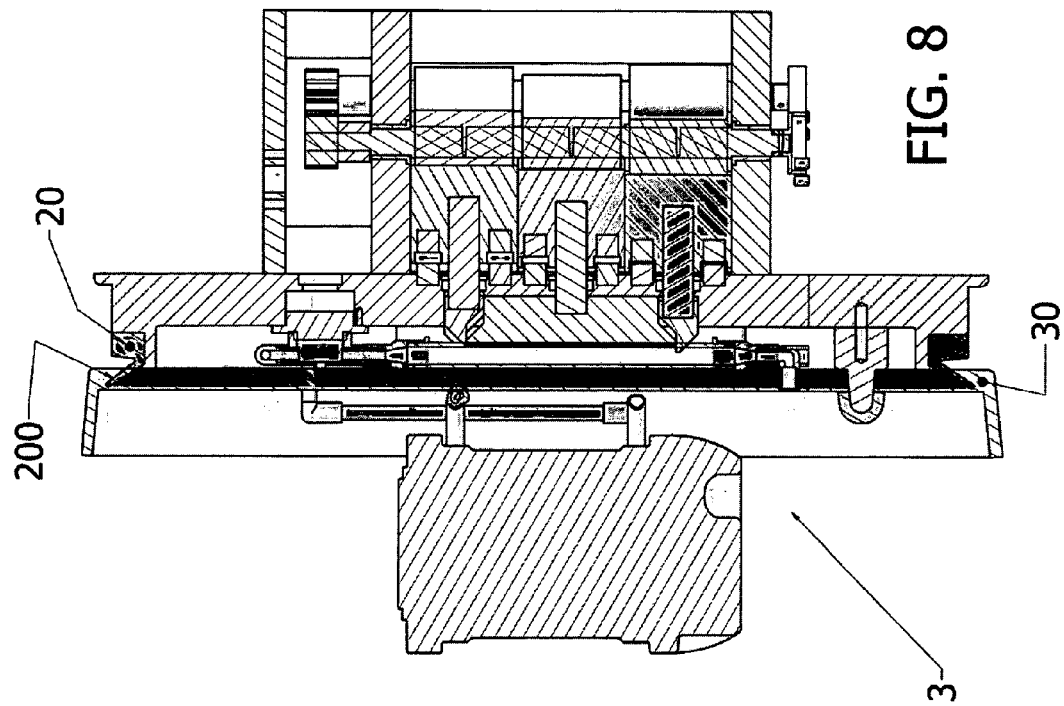
FIGS. 7, 8 are sectional views along the line C-C of FIG. 5 relating to two configurations of the machine, in which the module and the base with the pump unit are represented, respectively, at an early stage of coupling (FIG. 7) and at an operational phase or limit phase, in which the two elements are tightly linked by the implemented depression.
Figure 8:
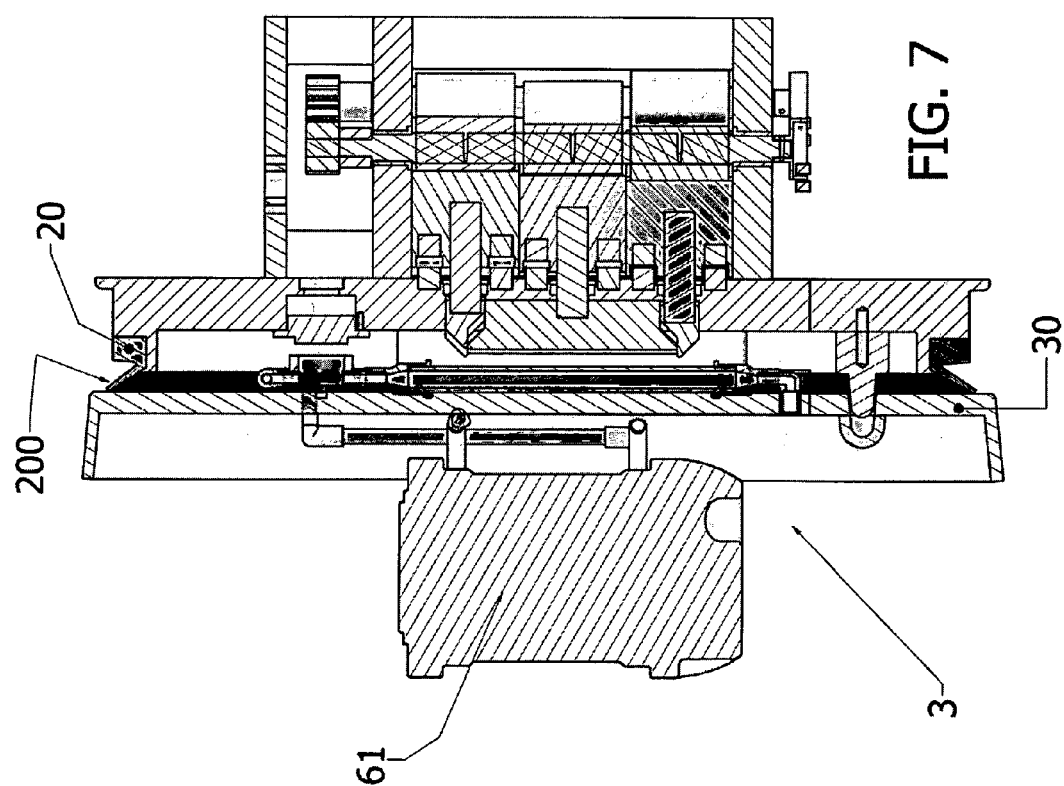

In FIGS. 7 and 8 is shown as the two parts 2 and 3 of the apparatus 1 are coupled. In practice, once chosen the disposable cartridge suitable for the therapy to be carried out, the disposable cartridge 3 is applied to the pump unit 2, thanks to the alignment determined by the correspondence between the spacers 21 and the seats 31. From a stage where both sides are completely separated, as shown in FIG. 6, there is the configuration shown in FIG. 7, where the ends 22 of spacers 21 is partially introduced in the seats 31 of the cartridge. As mentioned above, the configuration will be the following: the frontal access pumps 25, 26, 27, supported by the base of the apparatus (pump unit 2), are coupled to the tube segments 35, 36, 37 containing the liquid to be moved, segments which are part of the disposable module 3; the pressure transducers 63 are in contact with the respective detectors 71 on the base/pump 2; the "clamp" 74 of the pump unit 2 are placed in contact with the tube segment to be occluded; the air bubble detectors 73 and blood detectors 72 are positioned on the corresponding portion of tube, . . . ; in other words, all the components of an element which need a coupling are associated with the corresponding components of the other element, in automatically way, so safe and easy.

Once the cartridge 3 has been manually placed by an operator on the base 2, the same operator activates the vacuum pump, for example by means of a touch control screen 14 provided on the structure 10; the screen can be of "touch screen" type. At this point, the depression created between the base 2 and the cartridge 3 determines a configuration similar to that shown in FIG. 8, where the ends 22 are fully received in seat 31. The lowering of pressure in the chamber under the atmospheric value determines the cohesion between the cartridge 3 and the pump unit 2 and at, the same time, it allows to push, when necessary, the portions of the tube against the pumps set; this operation would be extremely difficult and is essentially impossible to safely obtain, if done manually.

The activation of the pump will be maintained until the desired depression, by detecting the pressure by means of the pressure switch which acts through the opening 76. The same pressure switch may be used for the surveys necessary for the maintenance of the depression suitable for the operation of the apparatus.

Due to the pressure which is lower than atmospheric pressure, the tubes which are pressed by the pumps, once the action of the pumps ends, easily return to their original configuration. This contributes to greater efficiency in the pumping, greater consistency of performance over time, with positive repercussions on the choice of materials and apparatus performance.

The seal between the base 2 and the cartridge 3 in the example has been realized through the gasket 20. There are still other possible forms of embodiment of the invention, differently conformed. For example, a connection can be made of telescopic type, with the base 2 or the cartridge 3 provide with cylindrical edges connected by means of coaxial cylindrical portions, sealed between them.

As mentioned above, the frontal access peristaltic pumps provided on the present apparatus allow the transportation of fluids within the relevant tubes, without requiring any intervention by the operator for the positioning, as, on the contrary, is required by conventional pumps. Moreover, by maintaining the pressure below a specified value, a greatly improved pumping action is allowed, allowing the use of thin-walled tubes which, otherwise, would not have an elastic memory sufficient to ensure the suction of liquids and the operation of the peristaltic pump. In practice, it is achieved a greater flow with the same outer diameter of the tube and with the same pump speed.

The pump of the invention is not a conventional peristaltic pump, nor a simple modification of a conventional peristaltic pump for the reasons listed below. In contrast to traditional peristaltic pumps, the portion of under-pump tubes is straight, which implies a benefit to the expansion caused by the vacuum even more.

The pipe is not "progressively pressed" by the rotor, but is pressed in a direction parallel to its axis in a sequence of three phases, while leaving a not compressed space in correspondence of the central pressing element.

The reaction plan of the pressing force of the tube is not a part of the pump but it is a part of the disposable cartridge.

The thin-walled tubes which are used would not work with traditional pumps because they aren't provided with the necessary elastic memory.

The vacuum also serves as a locking and mechanical coupling means between the pump and tube and also makes it possible the coupling of the accessory elements. In the embodiment shown, the pumps are three and are of a linear type with a plurality of pressing elements; of course, the solution which ensures the best operation of the pump due to the decrease in pressure is also applicable to other types of apparatuses including one or more pumps that operate on portions of tube contained and/or supported by disposable cartridges. In addition, the command and control devices of the elements described above and illustrated in the attached drawings are of the type known to the skilled in the art and, therefore, are not described in further detail for simplicity. Furthermore, the details of implementing information may change as equivalent in form, size, arrangement of elements, type of materials used, without leaving the area of the idea of the solution adopted and therefore remaining within the limits of the protection afforded by this patent.

The invention claimed is:

1. An apparatus for flowing fluids, comprising:
a base,
at least one pump in communication with said base,
a cartridge including a cartridge wall,
a seal member on the base and corresponding in shape to a perimeter presented by the cartridge, and
at least one tube in communication with said cartridge,
said seal member, said base and said cartridge forming a chamber so that both said at least one pump and said tube are disposed within said chamber, and said at least one pump is disposed against said tube and configured to create a fluid flow through the tube, and wherein there is a hole communicating with the chamber and applying a vacuum thereto so that the pressure inside said chamber is lower than atmospheric pressure.

2. Apparatus according to claim 1, wherein said scaling member includes a protrusion extending outwardly.

3. Apparatus according to claim 1, share wherein said base and said cartridge are in communication via a telescopic connection comprising coaxial cylindrical portions sealed together.

4. Apparatus according to claim 1, provided additionally comprising: a plurality of spacers or positioning elements arranged on said apparatus according to a predetermined disposition, said cartridge being provided with seats destined to receive said spacers and disposed according a disposition corresponding to the disposition of said spacers, disposition that allows only one type of coupling between spacers and seats.

5. Apparatus according to claim 4, wherein said spacers comprise a tapered end configured for fitting into a corresponding seat of said cartridge.

6. Apparatus according to claim 4, wherein said plurality of spacers include three spacers, with said spacers arranged according to a scalene triangle.

7. Apparatus according to claim 1, wherein said at least one pump includes at least one pressing element and said cartridge wall includes a reaction surface for said at least one pressing element.

8. Apparatus according to claim 1, wherein said at least one pump is provided with a plurality of pressing elements arranged along a straight section of said tube and wherein said pressing elements extend linearly.

9. Apparatus according to claim 1, additionally comprising: a supporting structure for supporting said base, said supporting structure including a flat portion defining a balance.

10. Apparatus according to claim 1, wherein said at least one pump includes at least a pressing element and said cartridge wall defines a reaction surface for said at least one pressing element.

11. Apparatus according to claim 2, wherein said at least one pump includes at least a pressing element and said cartridge wall includes a reaction surface for said at least one pressing element.

12. Apparatus according to claim 3, wherein said at least one pump includes at least a pressing element and said cartridge wall includes a reaction surface for said at least one pressing element.

13. Apparatus according to claim 4, wherein said at least one pump includes at least a pressing element and said cartridge wall includes a reaction surface for said at least one pressing element.

14. Apparatus according to claim 5, wherein said at least one pump includes at least a pressing element and said cartridge wall includes a reaction surface for said at least one pressing element.

15. Apparatus according to claim 6, wherein said at least one pump includes a pressing element and said cartridge wall includes a reaction surface for said at least one pressing element.

16. Apparatus according to claim 1, wherein said base includes a plurality of bars which extend beyond the height of said pump, said bars in communication with said cartridge wall.

\* \* \* \* \*